United States Patent [19]

Wittebrood et al.

[11] Patent Number: 5,352,681
[45] Date of Patent: Oct. 4, 1994

US005352681A

[54] PHARMACEUTICAL ENEMA PREPARATION

[75] Inventors: Adrianus Wittebrood, Velserbroek; Adrianus P. De Jong, Driehuis; Jan Bron, Giessenburg, all of Netherlands

[73] Assignee: BYK Nederland BV, Zwanenburg, Netherlands

[21] Appl. No.: 157,155

[22] PCT Filed: Jun. 5, 1992

[86] PCT No.: PCT/EP92/01274
§ 371 Date: Dec. 7, 1993
§ 102(e) Date: Dec. 7, 1993

[87] PCT Pub. No.: WO92/21324
PCT Pub. Date: Dec. 10, 1992

[30] Foreign Application Priority Data

Jun. 7, 1991 [CH] Switzerland ............... 01690/91-4
Jul. 5, 1991 [DE] Fed. Rep. of Germany ....... 4122337

[51] Int. Cl.$^5$ ............... A61K 31/60; A61K 31/615; A61K 9/08; B65D 81/24
[52] U.S. Cl. ............................................. 514/166
[58] Field of Search ......................................... 514/166

[56] References Cited

U.S. PATENT DOCUMENTS

| Re. 34,145 | 12/1992 | Martin | 523/205 |
|---|---|---|---|
| 3,658,552 | 4/1972 | Carlson et al. | 99/78 |
| 3,992,215 | 11/1976 | Su et al. | 106/287 |
| 4,034,079 | 7/1977 | Schooman | 424/83 |
| 4,137,092 | 1/1979 | Cumpston | 106/288 |
| 4,564,518 | 1/1986 | Rosenbaum | 424/9 |
| 4,657,900 | 4/1987 | Powell et al. | 514/166 |
| 4,664,256 | 5/1987 | Halskov | 206/213.1 |
| 4,771,086 | 9/1988 | Martin | 523/205 |
| 5,290,352 | 3/1994 | Krockert et al. | 106/436 |
| 5,298,065 | 3/1994 | Hiraoka et al. | 106/425 |

FOREIGN PATENT DOCUMENTS

| 291159 | 11/1988 | European Pat. Off. |
| 395329 | 10/1990 | European Pat. Off. |
| 398207 | 11/1990 | European Pat. Off. |
| 2647344 | 11/1990 | France |

*Primary Examiner*—Shep K. Rose
*Attorney, Agent, or Firm*—Jacobson, Price, Holman & Stern

[57] ABSTRACT

The light, oxidation and storage stability of aqueous 5-ASA suspensions is increased by incorporating in such suspensions an effective amount of titanium dioxide. The resulting stabilized aqueous suspensions are suitable for enema preparations.

5 Claims, No Drawings

PHARMACEUTICAL ENEMA PREPARATION

TECHNICAL FIELD

The invention relates to an enema preparation for 5-aminosalicylic acid.

PRIOR ART

5-Aminosalicylic acid (5-ASA) is a known active compound which is employed, in particular, for the treatment of inflammatory intestinal disorders, such as ulcerative colitis. The administration of 5-ASA as an enema preparation is particularly convenient, since the active principle can hereby be brought directly to the site of the pathological changes. In these preparations, however, the known chemical instability of 5-ASA in solutions or suspensions presents considerable difficulties. In the past, various paths were followed to get to grips, in particular, with the light and oxygen sensitivity of 5-ASA.

U.S. Pat. No. 4,657,900 thus proposes an enema preparation in which highly pure 5-ASA is present as an aqueous suspension which, after preparation with exclusion of oxygen and addition of bisulphite as an anti-oxidant, is sealed into an opaque polyethylene rectal applicator which, for its part, is heat-sealed into a polyester-/aluminum film/polyethylene bag.

U.S. Pat. No. 4,664,256 discloses a very similar administration form in which, apart from bisulphite, a chelating agent, such as, e.g., ethylenediaminetetraacetate (EDTA), is additionally contained as an antioxidant.

The problem of instability in enema preparations is apparently reasonably solved by these measures.

Apart from the expensive packing in the case of the 5-ASA enema preparations according to the prior art, the preparations, however, exhibit problems which have to do with the resuspendability of the 5-ASA suspension before use. The known preparations must be shaken very vigorously and persistently, especially before use, in order to achieve a homogeneous dispersion of the active compound which is desirable for administration. It goes without saying that this laborious resuspension is only managed inadequately, in particular by infirm patients and on the whole is not conducive to patient compliance.

DESCRIPTION OF THE INVENTION

It has now surprisingly been found that 5-ASA enema preparations according to the prior art can be improved in numerous respects by the addition of titanium dioxide. The light and oxidation stability of 5-ASA suspensions is increased by this addition according to the invention to such an extent that it is no longer necessary to make the 5-ASA suspension available in a double-walled container. A further advantage is that the stability of the suspension is increased such that the tiresome resuspension before administration by shaking can be dispensed with.

The invention therefore relates to an aqueous 5-aminosalicylic acid enema suspension preparation, which comprises titanium dioxide in addition to the customary auxiliaries.

Customary auxiliaries are understood as meaning those auxiliaries which are customarily employed for suspensions and those which can be used for the stabilization of 5-ASA suspensions. The first group includes, e.g., the customary viscosity-enhancing substances, preservatives, such as e.g. benzoic acid, pH, regulating substances, such as buffers; chelating agents, such as, e.g. EDTA; and antioxidants, such as, in particular, the bisulphites customary in 5-ASA preparations.

Titanium dioxide is added according to the invention in an amount of from 0.1 to 3, preferably from 0.1 to 1, and, in particular, 0.5% by weight.

5-ASA is contained in the suspensions according to the invention in an amount of from 0.5 to 10, preferably 2 to 6, and, in particular, about 4% by weight.

Bisulphites as antioxidants are contained in the suspensions according to the invention in an amount of from 0.05 to 0.5, preferably from 0.1 to 0.2, and, in particular, about 0.15% by weight.

Viscosity-enhancing substances are contained in the suspensions according to the invention in an amount of from 0.05 to 2, preferably from 0.1 to 1, and, in particular, about 0.5% by weight.

Chelating agents are contained in the suspension according to the invention in an amount of from 0.01 to 0.5, preferably from 0.05 to 0.2, and, in particular, about 0.1% by weight.

The suspension according to the invention is prepared according to the processes known from the prior art with the exclusion of oxygen. The finished suspension is then packed with exclusion of oxygen in customary flexible enema applicators, which are preferably manufactured from opaque plastic.

Preparation Example

A suspension is prepared according to the customary processes and packed in enema containers which, per 0 g enema pack, contain the following constituents:

| | |
|---|---|
| 5-aminosalicylic acid | 2.000 g |
| sodium dihydrogen phosphate × 2H$_2$O | 0.500 g |
| sodium edetate | 0.050 g |
| benzoic acid | 0.100 g |
| titanium dioxide E 171 | 0.250 g |
| sodium disulphite | 0.075 g |
| xanthan gum | 0.250 g |
| sodium hydroxide solution 10 M (to pH | 4.0) |
| purified water to | 50.00 g |

We claim:
1. An aqueous 5-aminosalicylic acid enema suspension preparation which comprises enema suspension preparation, which titanium dioxide in addition to customary enema suspension auxiliaries.

2. A preparation as claimed in claim 1, which contains 0.1 to 3% by weight of titanium dioxide.

3. The preparation as claimed in claim 1, which contains 5-aminosalicylic acid in an amount of from 0.5 to 10% by weight.

4. A preparation as claimed in claim 1, wherein in each enema suspension auxiliary is a member selected from the group consisting of a viscosity-enhancing substance, preservative, chelating agent, buffer and antioxidant.

5. An aqueous suspension comprising 5-amino salicylic acid in combination with a light and oxidation stabilizing amount of titanium dioxide.

* * * * *

UNITED STATES PATENT AND TRADEMARK OFFICE
CERTIFICATE OF CORRECTION

PATENT NO. : 5,352,681
DATED : October 4, 1994
INVENTOR(S) : Adrianus Wittebrood, et al It is certified that error appears in the above-indentified patent and that said Letters Patent is hereby corrected as shown below:

Column 2, line 4, "benzoic acid," should read --benzoic acid;-- "pH, regulating" should read --pH-regulating--; line 6, "e.g." should read --e.g.,--; line 35, "0" should read --50--; Column 2, line 48, "5-aminosalicylic acid enema" should read --enema--; line 2, "preparation" should read --preparation,--; lines 2 and 3, "enema suspension preparation, which" should read --5-aminosalicylic acid and--; Column 2, line 54, "The" should read --A--.

Signed and Sealed this

Tenth Day of January, 1995

Attest:

BRUCE LEHMAN

Attesting Officer

Commissioner of Patents and Trademarks